United States Patent
Kuth

(10) Patent No.: US 6,697,765 B2
(45) Date of Patent: Feb. 24, 2004

(54) METHOD AND MEDICAL SYSTEM FOR IMPROVED UTILIZATION OF A MEDICAL APPLIANCE, AND MEDICAL APPLIANCE

(75) Inventor: Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 193 days.

(21) Appl. No.: 10/072,908

(22) Filed: Feb. 12, 2002

(65) Prior Publication Data

US 2002/0128869 A1 Sep. 12, 2002

(30) Foreign Application Priority Data

Feb. 12, 2001 (DE) .......................... 101 06 305

(51) Int. Cl.[7] .............................................. G06F 19/00
(52) U.S. Cl. ............................. 702/188; 340/540; 705/2
(58) Field of Search ..................... 702/188, 182, 702/183, 184; 705/2, 7, 8; 340/500, 540, 679

(56) References Cited

U.S. PATENT DOCUMENTS

| | | | |
|---|---|---|---|
| 5,678,568 A | | 10/1997 | Uchikubo et al. |
| 6,216,054 B1 | * | 4/2001 | Jang et al. .................. 700/121 |
| 6,325,540 B1 | * | 12/2001 | Lounsberry et al. ........ 378/207 |
| 6,381,557 B1 | * | 4/2002 | Babula et al. ............... 702/183 |
| 6,412,980 B1 | * | 7/2002 | Lounsberry et al. ........ 378/207 |
| 6,516,324 B1 | * | 2/2003 | Jones et al. .............. 707/104.1 |
| 6,574,518 B1 | * | 6/2003 | Lounsberry et al. ........... 700/90 |
| 6,581,069 B1 | * | 6/2003 | Robinson et al. ........ 707/104.1 |
| 6,598,011 B1 | * | 7/2003 | Koritzinsky et al. ......... 702/185 |
| 2002/0004798 A1 | * | 1/2002 | Babula et al. ............ 707/104.1 |
| 2002/0120467 A1 | * | 8/2002 | Buanes .......................... 705/2 |
| 2002/0188652 A1 | * | 12/2002 | Goldhaber et al. .......... 709/201 |
| 2003/0014425 A1 | * | 1/2003 | Accardi et al. ......... 707/103 R |
| 2003/0025602 A1 | * | 2/2003 | Medema et al. .......... 340/568.1 |
| 2003/0050794 A1 | * | 3/2003 | Keck .............................. 705/2 |

FOREIGN PATENT DOCUMENTS

DE 199 11 699 9/2000

* cited by examiner

*Primary Examiner*—Patrick Assouad
(74) *Attorney, Agent, or Firm*—Young & Thompson

(57) ABSTRACT

A method and a system for improved utilization of a medical appliance (11, 21, 31, 41, 51), having elements (14, 22, 32, 42, 52) for determining the operating status of the medical appliance, elements (14, 22, 32, 42, 52) for transmitting the operating status to a central location (70), elements (71) for determining the time during which the medical appliance (11, 21, 31, 41, 51) is not used, and elements (71, 77) for notifying at least one person (13, 43, 61, 73, 81, 91, 101) when the time duration exceeds a predefined value. The invention additionally relates to a medical appliance (11, 21, 31, 41, 51) having elements (14, 22, 32, 42, 52) for determining its operating status.

22 Claims, 3 Drawing Sheets

METHOD AND MEDICAL SYSTEM FOR IMPROVED UTILIZATION OF A MEDICAL APPLIANCE, AND MEDICAL APPLIANCE

The invention relates to a method and a medical system for improved utilization of a medical appliance. The invention additionally relates to a medical appliance.

The highest possible utilization of expensive medical appliances, such as computer tomographs or magnetic resonance appliances, is worth striving for for reasons of return on investment. Inadequacies in the co-ordination of appointments of patients who are to be examined with such an appliance result from time to time in times during which the medical appliance remains unused, which in turn has a negative effect on the return on investment. In DE 119 11 699 A1, for example a method is disclosed for monitoring, controlling and optimizing process plans or working sequence plans, in that on the basis of process plans or working sequence plans already registered, the actual state of working units and an intended process plan or intended working project plan for a working unit are registered by means of stating performance features. On the basis of the actual state, the intended state or the performance features, a modified process plan or working sequence plan is then drawn up for the working unit.

U.S. Pat. No. 5,678,568 described a medical control system by means of which settings and operating states of a plurality of medical appliances connected to the control system can be indicated and changed.

The object of the invention is therefore a method for improved utilization of a medical appliance, having the following method steps:

a) registering the operating status of the medical appliance,
b) transmitting the operating status to a central location,
c) on the basis of the transmitted operating status, continuously determining the time during which the medical appliance has not been used, and
d) notifying at least one person when the time duration exceeds a predefined value.

The method according to the invention is therefore characterized in that the operating status of the medical appliance is determined and transmitted to a central location. The operating status comprises, for example, statements as to whether the appliance is used or not used. The appliance is used when an examination is carried out on a patient by means of the appliance. These statements can, for example, be noted by an operator of the medical appliance and transmitted to the central location, for example each time the operating status changes. At the central location, the time during which the medical appliance has not been used is then determined. This information can, for example, be used for statistical purposes, or, according to the invention, when the time during which the medical appliance is not used is exceeded by a predefined value, at least one person is notified, that is to say when the medical appliance remains unused for too long, a person, for example a coordinator for appointments for examinations of patients, is informed, so that the latter improves the coordination of the appointments, and therefore the utilization of the medical appliance is increased.

According to one embodiment of the invention, the operating status of the medical appliance comprises statements as to whether the medical appliance is occupied, occupied and activated, occupied but not activated and/or not occupied. The medical appliance is occupied when data from a patient who is examined with the medical appliance have been input into or called up from a computer associated with the medical appliance for the examination, so that an examination of the patient can be carried out with the medical appliance. The appliance is not occupied when the examination has been completed. "Occupied and activated" is understood to mean that the actual examination, that is to say a measurement with the medical appliance, is being carried out and "occupied but not activated" is understood to mean that although the data about the patient has been input into or called up from the computer associated with the medical appliance, the actual examination has not yet been started or has been interrupted. The sum of the times during which the medical appliance is occupied and activated and is occupied but not activated therefore corresponds to the time during which the medical appliance is occupied.

According to a variant of the invention, the time during which the medical appliance is not used corresponds to the time during which the medical appliance is not occupied or is occupied but not activated. The time during which the medical appliance is occupied but not activated permits, for example, conclusions to be drawn about the effective operation of the medical appliance. An increased time during which the medical appliance is not occupied permits conclusions to be drawn about a lack of coordination of examination appointments.

In order to evaluate the operating status, in particular statistically, according to one embodiment of the invention, the central location is assigned a database, in which data associated with the operating status is stored.

According to an advantageous variant of the invention, a supervisor monitors the operating status at the central location and informs the person when the time during which the medical appliance is not used exceeds the predefined value.

The supervisor can monitor the operating status particularly beneficially if, according to a further variant of the invention, the operating status is displayed graphically. For example, the operating status can be reproduced over a time axis, so that the supervisor recognizes times during which the medical appliance is not used and times during which the medical appliance is used in a simple manner. Therefore, for example, the supervisor can rapidly detect when the time during which the medical appliance is not used exceeds the predefined value, in order that he or she can notify the person or the persons.

A further embodiment of the invention is particularly advantageous, if the central location is assigned an evaluation device, which monitors the operating status and notifies the person when the time during which the medical appliance is not used exceeds the predefined value. Therefore, for example, the supervisor is assisted by a machine, or the supervisor can be dispensed with entirely.

The person who is notified when the time during which the medical appliance is not used has exceeded the predefined value is, according to a further embodiment of the invention, associated with a ward, a research department, an operator organization of the medical appliance, a hospital management or is an operator of the medical appliance. For example, provision is made that, when the time during which the medical appliance is occupied but not activated exceeds a first predefined value, contact is made with the operator in order, for example, to find out whether he or she has problems with the operation of the medical appliance. If this time duration exceeds a second, greater predefined value, for example the operator's supervisor is informed, in order that he or she trains the operator better, for example. Should the time during which the medical appliance is not occupied exceed a further predefined value, a person belonging to a ward can also be notified, in order that he or she organizes an examination with the medical appliance of a patient associated with this ward. Alternatively, a person in a research department can also be informed, for example after consultation with the operator, that the medical appliance is available for research purposes. In the event that a still longer predefined time duration is exceeded, an arrangement is also made to inform a person belonging to the hospital management.

Particularly reliable monitoring of the operating status is provided if, according to a further variant of the invention, the medical appliance determines its operating status automatically. In particular if the operating status is determined with computer assistance, then given suitable computer linking, it is possible to transmit the operating status continuously to the central location in a straightforward manner.

According to a variant of the invention, the medical appliance is an X-ray appliance, a computer tomograph, a magnetic resonance appliance, an ultrasound appliance or a lithotripter. These appliances in particular are expensive, and good utilization is worth striving for.

The object of the invention is also achieved by a system for improved utilization of a medical appliance having a first computer for determining the operating status of the medical appliance, means for transmitting the operating status to a central location, a second computer for continuously determining the time during which the medical appliance has not been used, and means for notifying at least one person when the time duration exceeds a predefined value. The system according to the invention is therefore designed in such a way that it can be used to carry out the method described above.

Further advantages of the invention emerge from the subclaims.

The object of the invention is also achieved by a medical appliance having means for determining whether the medical appliance is occupied, occupied and activated, occupied but not activated and/or not occupied. Such a medical appliance makes it possible to determine its operating status automatically in a simple way. A use of such a medical appliance for the method mentioned above facilitates carrying out the method.

Further advantages of the invention emerge from the subclaims.

An exemplary embodiment of the invention is illustrated in the appended schematic drawings, in which.

Figure 1:
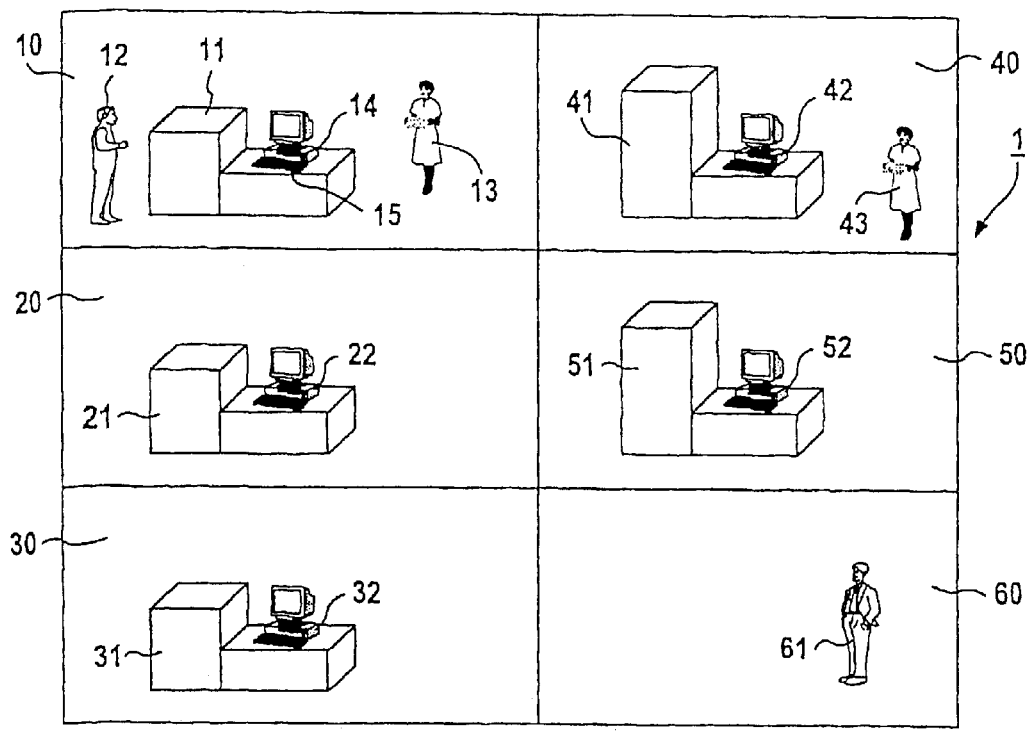
FIG. 1 shows a system according to the invention.
Figure 1:
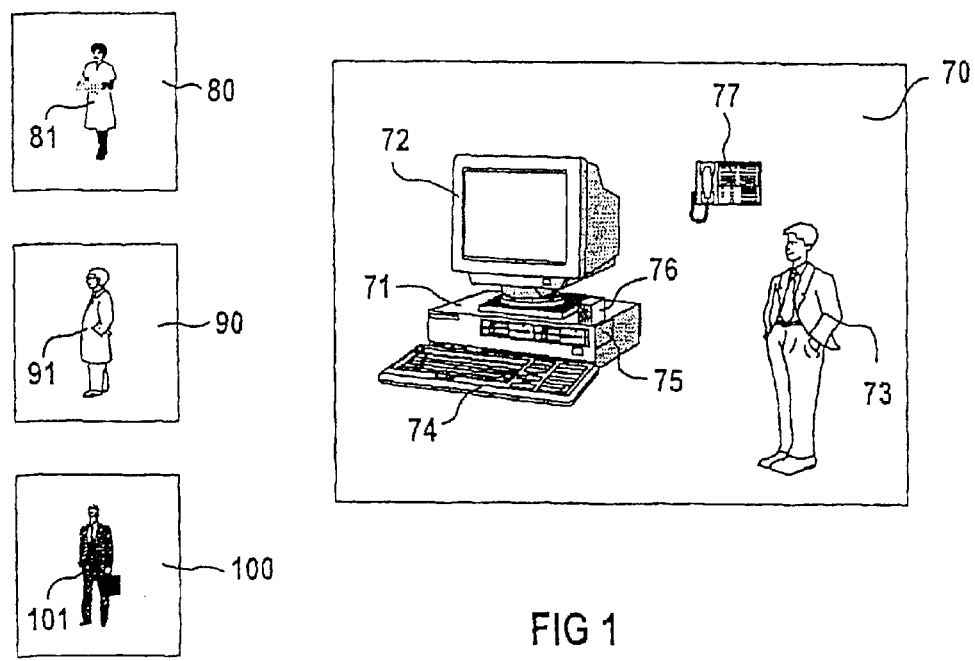

FIG. 1 shows, by way of example, a system for improved utilization of medical appliances, using which the method according to the invention will also be described as an example. FIG. 1 shows, schematically, a department 1 of a hospital. This department 1 comprises a plurality of rooms 10, 20, 30, 40 and 50, in which there are various medical appliances. In the case of the present invention, a magnetic resonance appliance 11 is arranged in room 10 of the department 1, a computer tomograph 21 in room 20, an ultrasound appliance 31 in room 30, a lithotripter 41 in room 40 and an X-ray appliance 51 in room 50.

When a patient 12 wishes to be subjected to an examination with the magnetic resonance appliance 11, he enters the room 10 and is greeted by an operator 13 of the magnetic resonance appliance 11. The operator 13 then enters the personal details of the patient 12 by using a keyboard 15 of a computer 14 of the magnetic resonance appliance 11, or calls up these personal details, if they are already stored in the computer 14. When the personal details are input or called up, in the case of the present exemplary embodiment the computer 14 automatically categorizes the operating status of the magnetic resonance appliance 11 as "occupied but not activated", since although the magnetic resonance appliance 11 is already being used, no measurement is yet being carried out with it.

After the personal details have been input or called up, the operator 13 describes the performance of the impending examination briefly to the patient 12. The examination with the magnetic resonance appliance 11 then begins, that is to say the magnetic resonance appliance 11 carries out a measurement, and the computer 14 automatically categorizes this new operating status of the magnetic resonance appliance 11 as "occupied and activated".

In particular if the examination comprises a number of partial examinations, in the case of the present exemplary embodiment, the operator 13 describes their performance briefly to the patient 12 before each partial examination. During the brief description, although the magnetic resonance appliance 11 is occupied, it is not carrying out a measurement, which is automatically recognized by the computer 14 as the operating status "occupied but not activated".

During the measurement of each partial examination, the computer 14 again automatically categorizes the operating status of the magnetic resonance appliance 11 as "occupied and activated".

In addition, the examination can also be interrupted since, for example, the operator 13 is undecided about the operation of the magnetic resonance appliance 11 or because he or she wishes to show pictures recorded with the magnetic resonance appliance 11 to a manager 61 of the department 1 who, in the case of the present exemplary embodiment, is in his office 60. These interruptions are likewise automatically recognized by the computer 14 as the operating status "occupied but not activated".

When the examination of the patient 12 has been completed, this is input into the computer 14, which automatically categorizes the new operating status of the magnetic resonance appliance 11 as "not occupied", so that the magnetic resonance appliance 11 is available for an examination of a further patient, not shown in FIG. 1.

Furthermore, in the case of the present exemplary embodiment, the computer 14 is connected to a computer network not shown in FIG. 1. At any change in the operating status of the magnetic resonance appliance 11, the computer 14 automatically transmits the new operating status with a statement of the time of the change to a computer 71 which is likewise connected to the computer network and is arranged in a monitoring room 70 belonging to the hospital. The data associated with the operating status is also stored in a database 75 belonging to the computer 71.

Figure 2:
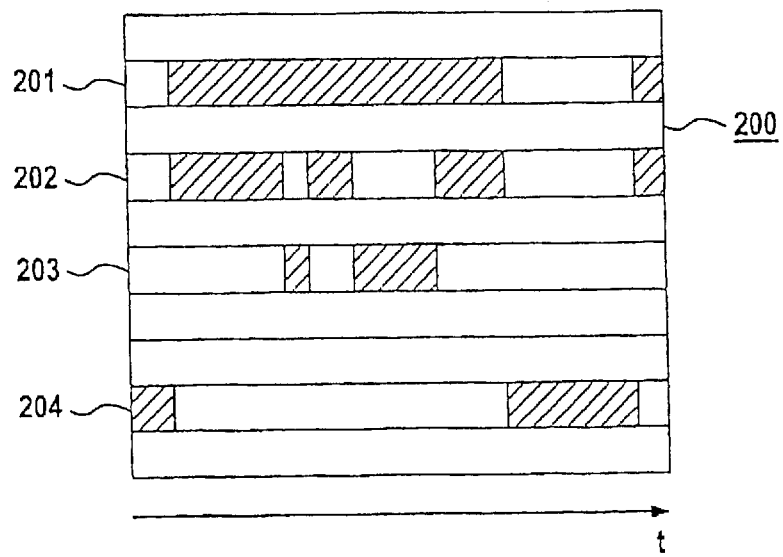
FIG. 2 shows a graphical representation of the operating status of a medical appliance.

By using a monitor 72 belonging to the computer 71, in the case of the present exemplary embodiment the time variation of the operating status of the magnetic resonance appliance 11 over the last 60 minutes is displayed graphically, as shown schematically in FIG. 2. The graphical representation comprises those items of information which have been transmitted to the computer 71 by the computer 14, that is to say statements and times at which the magnetic resonance appliance 11 is occupied and activated, occupied but not activated and not occupied. In addition, the monitor 72 indicates the time variation of the operating status during which the magnetic resonance appliance 11 is occupied. This time variation results as overlapping of the time variations of the operating status "occupied and activated" and the operating status "occupied but not activated". In the case of the present exemplary embodiment, these items of information are visualized by means of a bar graph 200, a bar 201 corresponding to a time period during which the magnetic resonance appliance 11 is occupied, a bar 202 corresponding to a time period during which it is occupied and activated, a bar 203 corresponding to a time period during which it is occupied but not activated, and a bar 204 corresponding to a time period during which it is not occupied. The supervisor 73 therefore has a quick overview of the time variation of the operating status of the magnetic resonance appliance 11 and can monitor the operating status in a simple way.

As already indicated, the department 1 of the hospital comprises further medical appliances accommodated in the rooms 20, 30, 40 and 50. Each of these medical appliances, that is to say the computer tomograph 21, the ultrasound appliance 31, the lithotripter 41 and the X-ray appliance 51, are each equipped with a computer 22, 32, 42 and 52, which automatically detect the respective operating status of their medical appliance and classify it in a similar way to the computer 14 of the magnetic resonance appliance 11. The computers 22, 32, 42 and 52 are likewise connected to the computer network and, at each change in an operating status, transmit the new operating status, with a statement of the time of the change, to the computer 71 arranged in the monitoring room 70. The data associated with each individual operating status of the medical appliances is likewise stored in the database 75 of the computer 71.

In addition, the time variation of the operating status, in each case associated with these medical appliances, can be displayed graphically by the monitor 72 of the computer 71. These time variations are displayed graphically in a similar way to the time variation of the operating status of the magnetic resonance appliance 11, as shown in FIG. 2. The supervisor 73 is able to select the desired display with the keyboard 74 of the computer 71, and therefore to monitor the time variation of the operating status of each medical appliance belonging to the department 1.

From the time variations of each individual transmitted operating status of the medical appliances, in the case of the present exemplary embodiment, for each medical appliance the computer 11 additionally automatically measures that time since which an examination of a patient with the corresponding medical appliance was completed and no new patient is yet occupying the corresponding medical appliance, that is to say the computer 71 continuously measures the current time during which the corresponding medical appliance has not been occupied. In addition, for each medical appliance, the computer 71 measures the time which has elapsed since the corresponding medical appliance was occupied but not activated. The supervisor 73 is able to select these items of information, that is to say the time durations, in the form of a schematic graphic 300 represented in FIG. 3, by using the keyboard 74, and to view them with the monitor 72. In the case of the present exemplary embodiment, the graphic comprises ten time-variable bars 301 to 310, which visualize the corresponding time durations of the medical appliances at the current time and become longer as the time duration increases. The bar 301 is associated with the time during which the magnetic resonance appliance 11 is not occupied, and the bar 302 is associated with the time during which the magnetic resonance appliance 11 is occupied but not activated. The bar 303 is associated with the time during which the computer tomograph 21 is not occupied, and the bar 304 is associated with the time during which the computer tomograph 21 is occupied but not activated. The bar 305 is associated with the time during which the ultrasound appliance 31 is not occupied, and the bar 306 is associated with the time during which the ultrasound appliance 31 is occupied but not activated. The bar 307 is associated with the time during which the lithotripter 41 is not occupied, and the bar 308 is associated with the time during which the lithotripter 41 is occupied but not activated. The bar 309 is associated with the time during which the X-ray appliance 51 is not occupied, and the bar 310 is associated with the time during which the X-ray appliance 51 is occupied but not activated. In the case of the present exemplary embodiment, for example, the magnetic resonance appliance 11 has not been occupied for five minutes.

Furthermore, in the case of the present exemplary embodiment, in the event of one of the time durations being exceeded by predefined values, provision is made for various persons to be notified of this fact. For this purpose, a suitable computer program is stored on the computer 71, compares these time durations with the predefined values and, in the event of a value being exceeded, generates an alarm signal with the aid of a loudspeaker 76 integrated into the computer 71. The supervisor 73 can then select the graphic 300 shown in FIG. 3 and detect which time duration has exceeded which value. He or she then informs the appropriate person.

If, in the case of the present exemplary embodiment, one of the medical appliances belonging to the department 1 is not occupied for longer than five minutes, the supervisor 73 is sent an alarm by means of the alarm signal and, by using a telephone 77 arranged in the monitoring room 70, telephones the operator of that medical appliance that has not been occupied for five minutes. If the appropriate operator cannot be reached by telephone, the supervisor 73 sends this operator an e-mail. In the case of the present exemplary embodiment, the magnetic resonance appliance 11 has not been occupied for five minutes, and the supervisor 73 makes contact by telephone with the operator 13 of the magnetic resonance appliance 11. In the case of the present exemplary embodiment, the supervisor 73 asks why the magnetic resonance appliance 11 is not occupied and, if necessary, arranges that a new patient can be examined with the magnetic resonance appliance 11.

If one of the medical appliances is not occupied for more than 15 minutes, in the case of the present exemplary embodiment, the supervisor 73 notifies the manager 61 of the department 1 of the hospital. In the case of the present exemplary embodiment, the computer tomograph 21 has not been occupied for 15 minutes. Since the manager 61 of the department 1 has been informed of this fact, he can himself find out the reasons and ensure that the computertomograph 21 or, in general terms, the medical appliances are utilized better. If, in the case of the present exemplary embodiment, the computertomograph 21 has not been occupied for longer than 15 min, since a patient not illustrated in FIG. 1 has not appeared for his envisaged examination, the manager 61 can remind a person 81 belonging to a ward 80 associated with this patient of the examination, in order to obtain good utilization of the computertomograph 21. If the manager 61 then learns that the examination for this patient has been canceled, he can also inform a scientist 91 of a research department 90 of the hospital about the availability of the computertomograph 21, so that the computertomograph 21 is at least used for research purposes.

If, in the case of the present exemplary embodiment, one of the medical appliances has not been occupied for longer than two hours, as is the case for the X-ray appliance 51, the supervisor 73 notifies a member 101 of the hospital management 100.

The supervisor 73 also informs persons in the event that the time during which one of the medical appliances is occupied but not activated is exceeded by predefined values.

Should one of the medical appliances be occupied but not activated for five minutes, the supervisor 73 telephones the operator of the corresponding medical appliance in order to find out whether there are problems with the corresponding appliance. In the case of the present exemplary embodiment, the ultrasound appliance 31 has been occupied but not activated for five minutes.

If one of the medical appliances has been occupied but not activated for 15 minutes, the supervisor 73 informs the manager 61 of the department 1 of the hospital. In the case of the present exemplary embodiment, the lithotripter has been occupied but not activated for 15 minutes. Consequently, the manager 61 can seek out an operator 43 of the lithotripter 41 in order, for example, to be helpful to him or her during the ongoing examination.

Should one of the medical appliances be occupied but not activated for two hours, the supervisor 73 again informs the person 101 belonging to the hospital management 100.

Figure 4:
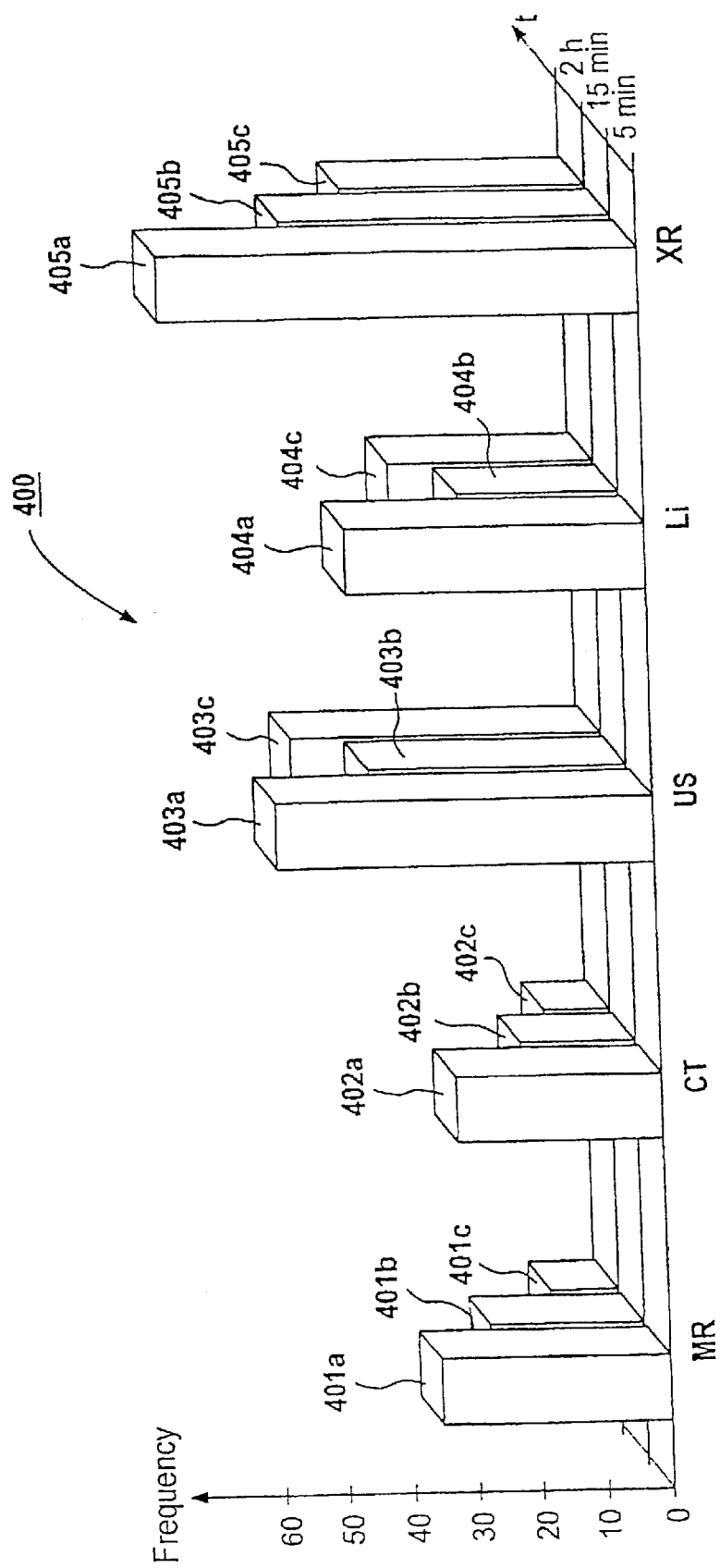
FIG. 4 shows a graphical representation of frequencies within a time period during which medical appliances were not used.

In particular for statistical purposes, the computer 71 generates a further graphic 400, which is represented schematically in FIG. 4 and can be selected with the keyboard 74. The graphic 400 shown in FIG. 4 indicates the frequency in bar form at which each of the medical appliances belonging to the department 1 of the hospital was not occupied for longer than five minutes, 15 minutes and two hours in a month. The bars 401a to 401c are associated with the magnetic resonance appliance 11, the bars 402a to 402c are associated with the computertomograph 21, the bars 403a to 403c are associated with the ultrasound appliance 31, the bars 404a to 404c are associated with the lithotripter 41 and the bars 405a to 405c are associated with the X-ray appliance 51. The bars 401a, 402a, 403a, 404a and 405a correspond to the frequency at which the corresponding medical appliance was not occupied for longer than five minutes, the bars 401b, 402b, 403b, 404b and 405b correspond to the frequency at which the corresponding medical appliance was not occupied for longer than 15 minutes, and the bars 401c, 402c, 403c, 404c and 405c correspond to the frequency at which the corresponding medical appliance was not occupied for longer than two hours, during a specific month. This graphic 400 is presented monthly to the person 101 belonging to the hospital management 100 and to the manager 61 of the department 1, so that they are informed about the utilization of the medical appliances belonging to the department 1 and, if necessary, can initiate steps for improved utilization of these appliances.

A supervisor 73 is not required for the system or method according to the invention. In the event of exceeding the times in which one of the appliances is not occupied or is occupied but not activated, the computer 71 can inform the persons described above automatically. Of course, these persons are mentioned only by way of example. In addition, the values at which, if they are exceeded, the persons are informed, are of an exemplary nature.

Automatic registration of the operating status with the computers (14, 21, 31, 41, 51) belonging to the medical appliances is likewise optional for the method or system of the invention. The operating status of each medical appliance can also be determined manually, for example by the respective operator, and transmitted, for example by telephone, to the supervisor 73, so that the supervisor 73 can, for example, enter this information into the computer 71. Nor does the operating status of each medical appliance necessarily have to be transmitted at each change in the operating status. This time variation can, for example, also be transmitted periodically, for example daily.

In addition, the above-described categorization of the operating status is to be understood as an example.

Figure 3:
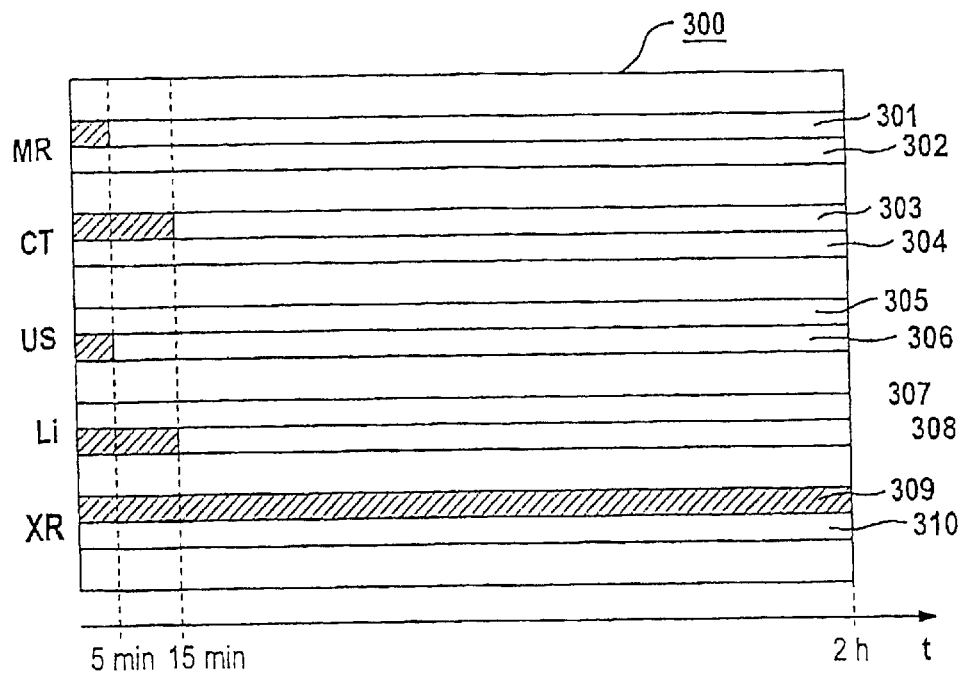
FIG. 3 shows a graphical representation of times during which medical appliances were not used.

A graphical display of the operating status is optional. The graphics 200, 300 and 400 represented in FIGS. 2 to 4 are likewise only of an exemplary nature.

The aforementioned medical appliances, magnetic resonance appliance 11, computertomograph 21, ultrasound appliance 31, lithotripter 41 and X-ray appliance 51 are likewise to be understood only as examples. Further medical appliances can also be monitored. The number of aforementioned medical appliances is also to be understood as an example. In particular, it is also possible for only one medical appliance to be monitored.

The medical appliances do not necessarily have to be associated with a department 1 or a hospital, either. The invention may also be useful for a doctor's practice, for example.

What is claimed is:

1. A method for improved utilization of a medical appliance, having the following method steps:
   a) registering the operating status of the medical appliance (11, 21, 31, 41, 51),
   b) transmitting the operating status to a central location (70),
   c) on the basis of the transmitted operating status, continuously determining the time during which the medical appliance (11, 21, 31, 41, 51) has not been used, and
   d) notifying at least one person (13, 43, 61, 73, 81, 91, 101) when the time duration exceeds a predefined value.

2. The method for improved utilization of a medical appliance as claimed in claim 1, in which the operating status comprises statements as to whether the medical appliance (11, 21, 31, 41, 51) is occupied, occupied and activated, occupied but not activated and/or not occupied.

3. The method for improved utilization of a medical appliance as claimed in claim 1, in which the time during which the medical appliance (11, 21, 31, 41, 51) is not used corresponds to the time during which the medical appliance (11, 21, 31, 41, 51) is not occupied and/or the medical appliance (11, 21, 31, 41, 51) is occupied but not activated.

4. The method for improved utilization of a medical appliance as claimed in claim 1, in which the central location (70) is assigned a database (75) in which data associated with the operating status is stored.

5. The method for improved utilization of a medical appliance as claimed in claim 1, in which a supervisor (73) monitors the operating status at the central location (70) and notifies the person (13, 61, 81, 91, 101) when the time during which the medical appliance (11, 21, 31, 41, 51) is not used exceeds the predefined value.

6. The method for improved utilization of a medical appliance as claimed in claim 1, in which the operating status is displayed graphically.

7. The method for improved utilization of a medical appliance as claimed in claim 1, in which the central location (70) is assigned an evaluation device (71), which monitors the operating status and notifies the person (21, 61, 73, 81, 91, 101) when the time during which the medical appliance (11, 21, 31, 41, 51) is not used exceeds the predefined value.

8. The method for improved utilization of a medical appliance as claimed in claim 1, in which the person (13, 43, 81, 91, 101) is associated with a ward (80), a research department (90), an operator organization of the medical appliance (11, 21, 31, 41, 51), a hospital management (100) or is an operator (13, 43) of the medical appliance (11, 41).

9. The method for improved utilization of a medical appliance as claimed in claim 1, in which the medical appliance (11, 21, 31, 41, 51) determines its operating status automatically.

10. The method for improved utilization of a medical appliance as claimed in claim 1, in which the medical appliance (11, 21, 31, 41, 51) is an X-ray appliance (51), a computertomograph (21), a magnetic resonance appliance (11), an ultrasound appliance (31) or a lithotripter (41).

11. A system for improved utilization of a medical appliance, comprising a first computer (14, 22, 32, 42, 52) for determining the operating status of the medical appliance (11, 21, 31, 41, 51), means for transmitting the operating status to a central location (70), a second computer (71) for continuously determining the time during which the medical appliance (11, 21, 31, 41, 51) has not been used, and means (71, 77) for notifying at least one person (13, 43, 61, 73, 81, 91, 101) when the time duration exceeds a predefined value.

12. The system for improved utilization of a medical appliance as claimed in claim 11, in which the operating status comprises statements as to whether the medical appliance (11, 21, 31, 41, 51) is occupied, occupied and activated, occupied but not activated and/or not occupied.

13. The system for improved utilization of a medical appliance as claimed in claim 11, in which the time during which the medical appliance (11, 21, 31, 41, 51) is not used corresponds to the time during which the medical appliance (11, 21, 31, 41, 51) is not occupied and/or the medical appliance (11, 21, 31, 41, 51) is occupied but not activated.

14. The system for improved utilization of a medical appliance as claimed in claim 11, in which the central location (70) is assigned a database (75) in which data associated with the operating status can be stored.

15. The system for improved utilization of a medical appliance as claimed in claim 11, in which a supervisor (73) monitors the operating status at the central location (70) and informs the person (13, 61, 81, 91, 101), using the means (71, 77) for notification, when the time during which the medical appliance (11, 21, 31, 41, 51) is not used exceeds the predefined value.

16. The system for improved utilization of a medical appliance as claimed in claim 11, in which the operating status can be displayed graphically.

17. The system for improved utilization of a medical appliance as claimed in claim 11, in which an evaluation device (71) is provided, which monitors the operating status and notifies the person (13, 61, 73, 81, 91, 101) when the time during which the medical appliance (11, 21, 31, 41, 51) is not used exceeds the predefined value.

18. The system for improved utilization of a medical appliance as claimed in claim 11, in which the person (13, 43, 81, 91, 101) is associated with a ward (80), a research department (90), an operator organization of the medical appliance (11, 21, 31, 41, 51), a hospital management (100) or is an operator (13, 43) of the medical appliance (11, 41).

19. The system for improved utilization of a medical appliance as claimed in claim 11, in which the medical appliance (11, 21, 31, 41, 51) comprises the first computer (14, 22, 32, 42, 52).

20. The system for improved utilization of a medical appliance as claimed in claim 11, in which the medical appliance (11, 21, 31, 41, 51) is an X-ray appliance (51), a computertomograph (21), a magnetic resonance appliance (11), an ultrasound appliance (31) or a lithotripter (41).

21. A medical appliance, having means (14, 22, 32, 42, 52) for determining whether the medical appliance (11, 21, 31, 41, 51) is occupied, occupied and activated, occupied but not activated and/or not occupied.

22. The medical appliance as claimed in claim 21, which is an X-ray appliance (51), a computertomograph (21), a magnetic resonance appliance (11), an ultrasound appliance (31) or a lithotripter (41).

* * * * *